United States Patent
Takii

(10) Patent No.: US 9,560,966 B2
(45) Date of Patent: Feb. 7, 2017

(54) NON-CONTACT TYPE TONOMETER

(71) Applicant: NIDEK CO., LTD., Aichi (JP)

(72) Inventor: Michihiro Takii, Aichi (JP)

(73) Assignee: NIDEK CO., LTD., Aichi (JP)

(*) Notice: Subject to any disclaimer, the term of this patent is extended or adjusted under 35 U.S.C. 154(b) by 315 days.

(21) Appl. No.: 14/037,861

(22) Filed: Sep. 26, 2013

(65) Prior Publication Data

US 2014/0092361 A1 Apr. 3, 2014

(30) Foreign Application Priority Data

Sep. 28, 2012 (JP) ................. 2012-217445
Sep. 28, 2012 (JP) ................. 2012-217446

(51) Int. Cl.
*A61B 3/16* (2006.01)
*A61B 3/10* (2006.01)

(52) U.S. Cl.
CPC ............ *A61B 3/165* (2013.01); *A61B 3/1005* (2013.01)

(58) Field of Classification Search
CPC ............ A61B 3/1005; A61B 3/16; A61B 3/10
USPC ................................. 351/211, 205
See application file for complete search history.

(56) References Cited

U.S. PATENT DOCUMENTS

| 5,474,066 A | 12/1995 | Grolman | |
|---|---|---|---|
| 2010/0030056 A1* | 2/2010 | Abramov | 600/401 |
| 2012/0220850 A1* | 8/2012 | Umekawa | 600/401 |

FOREIGN PATENT DOCUMENTS

| JP | 08-507463 | 8/1996 |
|---|---|---|
| JP | 2002-102170 | 4/2002 |
| WO | 95/20342 | 8/1995 |

* cited by examiner

*Primary Examiner* — Bumsuk Won
*Assistant Examiner* — Grant Gagnon
(74) *Attorney, Agent, or Firm* — Rankin, Hill & Clark LLP

(57) ABSTRACT

A non-contact type tonometer includes: a measurement unit including a first measuring unit for measuring an eye pressure of an examinee's eye in a non-contact manner and a second measuring unit for measuring a corneal thickness of the examinee's eye in a non-contact manner; a moving mechanism for causing relative movement of the measurement unit with respect to the examinee's eye; a drive controller for driving the moving mechanism for aligning the measurement unit; and a setting switch controller for switching an alignment reference on the cornea used for aligning the measurement unit between first and second alignment references. The first alignment reference is a reference for measuring the eye pressure with the first measuring unit and the second alignment reference is a reference for measuring the corneal thickness with the second measuring unit and set closer to a corneal rear surface than the first alignment reference.

10 Claims, 6 Drawing Sheets

NON-CONTACT TYPE TONOMETER

CROSS-REFERENCE TO RELATED APPLICATION

This application claims priority from Japanese Patent Applications No. 2012-217445 and 2012-217446 filed with the Japan Patent Office on Sep. 28, 2012, the entire content of which are hereby incorporated by reference.

BACKGROUND

1. Technical Field

The present disclosure relates to a non-contact type tonometer.

2. Related Art

A non-contact type tonometer measures the eye pressure of an examinee's eye in a non-contact manner. Specifically, the non-contact type tonometer first sprays a liquid onto the cornea of the examinee's eye via a nozzle. The non-contact type tonometer then optically detects a deformed state of the cornea upon the spraying of liquid. In this way, the non-contact type tonometer measures the eye pressure of the examinee's eye based on the deformed state of the cornea in a non-contact manner. A known example of such a non-contact type tonometer is an apparatus including an optical system for measuring the corneal thickness of the examinee's eye. The apparatus corrects the eye pressure value of the examinee's eye based on an obtained measurement result (see, for example, JP-A-8-507463).

An apparatus described in JP-A-2002-102170 causes a light flux to obliquely enter the examinee's eye during measurement of the corneal thickness. Reflected light from the cornea is received by a light receiving device, such as a line sensor. The apparatus measures the corneal thickness based on a peak value of a light receiving signal for reflected light from front and rear surfaces of the cornea. In the apparatus, alignment in an actuation distance direction is conducted with reference to the peak value of the light receiving signal for the reflected light from the corneal front surface, during both eye pressure measurement and corneal thickness measurement.

SUMMARY

A non-contact type tonometer includes: a measurement unit including a first measuring unit configured to measure an eye pressure of an examinee's eye in a non-contact manner and a second measuring unit configured to measure a corneal thickness of the examinee's eye in a non-contact manner: a moving mechanism configured to cause relative movement of the measurement unit with respect to the examinee's eye; a drive controller configured to drive the moving mechanism for aligning the measurement unit; and a setting switch controller configured to switch an alignment reference on the cornea used for aligning the measurement unit between a first alignment reference and a second alignment reference. The first alignment reference is a reference for measuring the eye pressure with the first measuring unit, and the second alignment reference is a reference for measuring the corneal thickness with the second measuring unit and set closer to a corneal rear surface than the first alignment reference.

DETAILED DESCRIPTION

Figure 1:
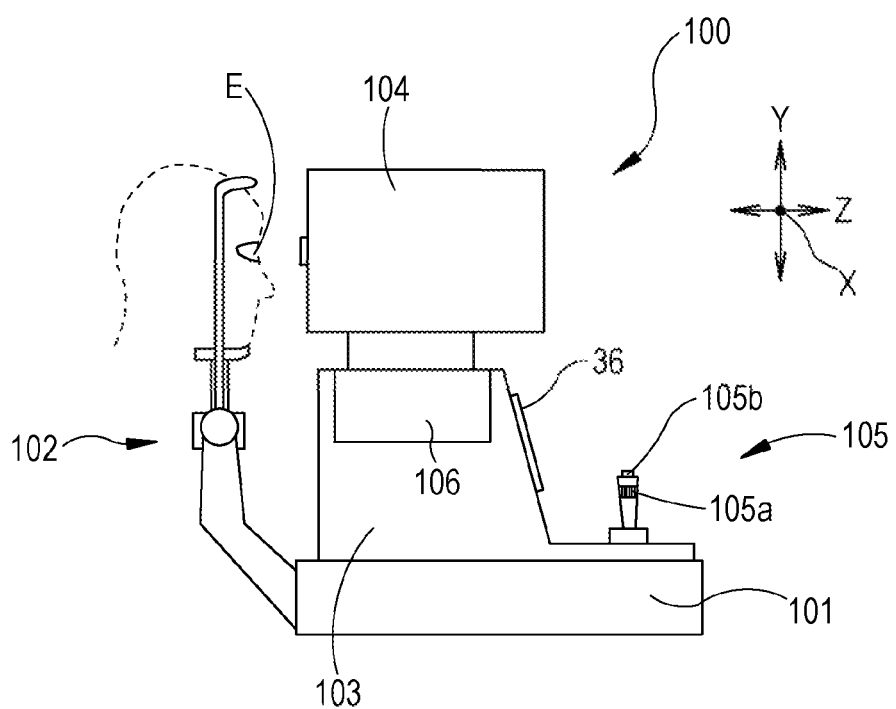
FIG. 1 is a schematic diagram illustrating an exterior appearance of an apparatus according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The amount of reflection from the rear surface of the cornea is small compared with the amount of reflection from the front surface of the cornea. When reflected light is received by a light receiving device, the peak of the reflected light from the rear surface is smaller than the peak of the reflected light from the front surface. The amount of light of the reflected light from the rear surface is further decreased when an alignment reference in the actuation distance direction is aligned with the corneal front surface. The greater the thickness of the cornea, the smaller the amount of light becomes. Therefore, when the reference position is aligned with the corneal front surface for alignment, as in a conventional apparatus, the peak of the reflected light from the corneal rear surface that is received by the light receiving device becomes smaller, resulting in a decrease in corneal thickness measurement accuracy.

An object of the present disclosure is to provide a non-contact type tonometer that can accurately measure the corneal thickness of the examinee's eye.

A non-contact type tonometer according to an embodiment of the present disclosure has the following configuration.

(1) A non-contact type tonometer includes: a measurement unit including an eye pressure measurement means including a first detector for detecting a reflection signal from a corneal front surface of the examinee's eye, a corneal thickness measurement means including a second detector for detecting the reflection signal from the corneal front surface and a reflection signal from a corneal rear surface, and an observing optical system for observing an anterior segment of the examinee's eye, the eye pressure measurement means measuring an eye pressure of the examinee's eye in a non-contact manner, the corneal thickness measurement means measuring a corneal thickness of the examinee's eye in a non-contact manner, and the observing optical system being used commonly for aligning the eye pressure measurement means and the corneal thickness measurement means in an up-down direction; a moving mechanism including an electric motor for relatively moving the measurement unit with respect to the examinee's eye; and an alignment detection means including a third detector disposed on the measurement unit for detecting a reflection signal from the cornea of the examinee's eye, the alignment detection means detecting an alignment state of the measurement unit with respect to the cornea of the examinee's eye in the front-rear direction. The alignment detection means switches an alignment reference position set on the cornea for detecting the alignment state between eye pressure measurement and corneal thickness measurement, and detects the alignment state with respect to the alignment reference position after the switching.

(2) In the non-contact type tonometer according to (1), the alignment detection means sets a first alignment reference position for measuring the eye pressure on the corneal front surface, and sets a second alignment reference position for measuring the corneal thickness on the corneal rear surface or in the vicinity of the corneal rear surface.

(3) In the non-contact type tonometer according to (1) and (2), a control means for moving the measurement unit toward the alignment reference position by controlling the electric motor based on a result of detection by the alignment detection means is provided.

(4) In the non-contact type tonometer according to (1) to (3), the alignment detection means, during corneal thickness measurement, detects the alignment state of the measurement unit with respect to the first alignment reference position set for the eye pressure measurement, and switches the alignment reference position to the second alignment reference position set for the eye pressure measurement in response to a measurement completion signal from the corneal thickness measurement means, and the control means causes the measurement unit to be moved from the first alignment reference position toward the second alignment reference position in a direction away from the examinee's eye, and successively measures the eye pressure and the corneal thickness of the examinee's eye in order.

(5) In the non-contact type tonometer according to (1) to (4), the control means causes the measurement unit to be moved in the direction away from the examinee's eye based on the corneal thickness obtained by the corneal thickness measurement, and causes the measurement unit to be moved based on a result of detection of the alignment state with respect to the second alignment reference position.

(6) In the non-contact type tonometer according to (1) to (5), the eye pressure measurement means includes, as the first detector, a liquid spraying means that sprays a liquid onto the cornea of the examinee's eye via a nozzle, and a deformation detection means that detects a deformed state of the cornea due to the liquid sprayed by the liquid spraying means.

(7) In the non-contact type tonometer according to (1) to (6), the eye pressure measurement means includes a first detector that detects the reflection signal from the corneal front surface of the examinee's eye by using ultrasound, and measures the eye pressure of the examinee's eye in a non-contact manner by using ultrasound.

(8) In the non-contact type tonometer according to (1) to (7), one detector is provided as a third detector and used for both the eye pressure measurement and the corneal thickness measurement, and the alignment detection means switches the alignment reference by discriminating between a reflection signal from the corneal rear surface and a reflection signal from the corneal front surface, both the reflection signals being included in the reflection signal from the cornea.

(9) In the non-contact type tonometer according to (1) to (8), different detectors are provided as third detectors and independently used for the eye pressure measurement and the corneal thickness measurement, and the alignment detection means switches the alignment reference by changing the detector used for detecting the alignment state.

(10) In the non-contact type tonometer according to (1) to (9), at least one of the first detector, the second detector, and the third detector is shared.

(11) In the non-contact type tonometer according to (1) to (10), the third detector detects the reflection signal from the cornea by receiving reflected light from the cornea of the examinee's eye, and the alignment detection means detects the alignment state with respect to the corneal anterior surface by detecting a position of the reflected light from the corneal anterior surface during eye pressure measurement, and detects the alignment state with respect to the corneal posterior surface by detecting a position of reflected light from the corneal rear surface during corneal thickness measurement.

(12) In the non-contact type tonometer according to (1) to (11), displays indicating the establishment of alignment are switched between eye pressure measurement and corneal thickness measurement.

The non-contact type tonometer according to an embodiment of the present disclosure can accurately measure the corneal thickness of the examinee's eye, and accurately correct the eye pressure value of the examinee's eye.

Hereinafter, an embodiment of the present disclosure will be described with reference to the drawings. FIG. 1 is a diagram illustrating an exterior appearance of a non-contact type tonometer according to the present embodiment.

The non-contact type tonometer (tonometer) 100 is of a so-called stationary type non-contact type tonometer. The tonometer 100) includes a base 101, a face support unit 102, a movable base 103, and a measurement unit 104. The face support unit 102 is attached to the base 101. The movable base 103 is movably disposed on the base 101. The measurement unit 104 is movably disposed on the movable base 103. The measurement unit 104 houses a measuring system and an optical system, which will be described later. The movable base 103 includes an XYZ drive unit (moving mechanism) 106. The measurement unit 104 is moved by the XYZ drive unit 106 in a left-right direction (X-direction), an up-down direction (Y-direction), and a front-rear direction (Z-direction) with respect to the examinee's eye E. An examiner operates a joystick 105 to cause the XYZ drive unit 106 to move the movable base 103 in the X-direction and the Z-direction on the base 101. The examiner rotates a rotating knob 105a to cause the XYZ drive unit 106 to move the measurement unit 104 in the Y-direction by Y-drive. At the top of the joystick 105, a measurement start switch 105b is disposed. The movable base 103 is provided with a display monitor 36.

Figure 2:
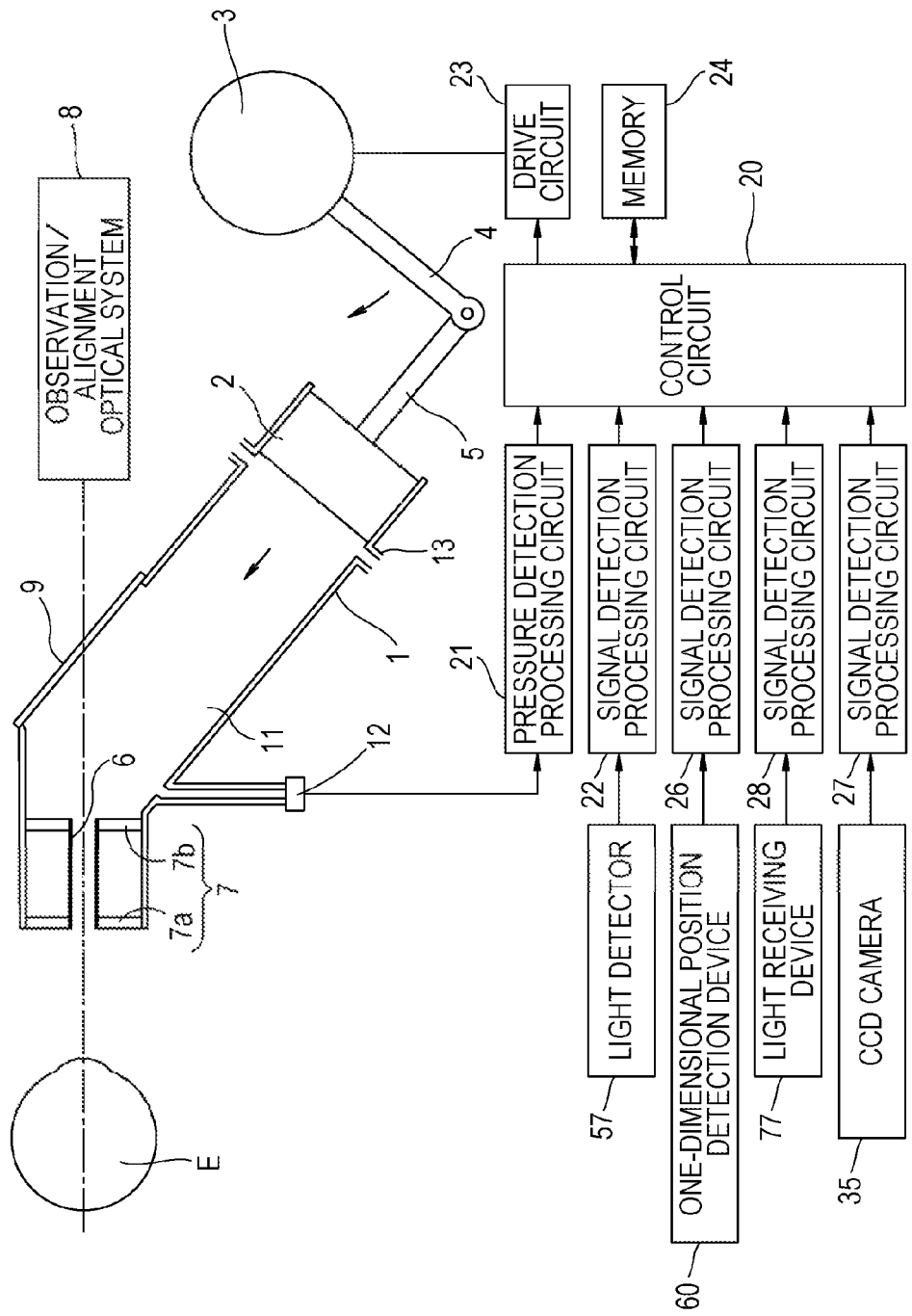
FIG. 2 is a schematic diagram illustrating a side view of a liquid discharge mechanism and main parts of a control system of the apparatus according to the embodiment.

FIG. 2 is a schematic diagram illustrating a side view of a liquid discharge mechanism and main parts of a control system of the tonometer 100. The liquid discharge mechanism is provided to the measurement unit 104. The control system may be provided to the measurement unit 104, the movable base 103, or the base 101.

The liquid discharge mechanism (a first measuring unit; a liquid spraying unit) of the tonometer 100 includes a cylinder portion 1, a rotary solenoid 3, an arm 4, a connecting rod (piston rod) 5, a nozzle 6, a transparent glass plate 7, a transparent glass plate 9, an air compression chamber 11, and a pressure sensor 12.

The cylinder portion 1 is provided for compressing air and inclined with respect to the horizontal line of the body of the tonometer 100. As the rotary solenoid 3 is supplied with electric charges as driving energy (current or voltage), the rotary solenoid 3 pushes the piston 2 upward along the cylinder portion 1 via the arm 4 and the connecting rod (piston rod) 5. The air compression chamber 11 is disposed in communication with the cylinder portion 1. As the piston 2 rises, air is compressed in the air compression chamber 11. The compressed air is ejected out of the nozzle 6 toward the cornea of the examinee's eye E. The rotary solenoid 3 is provided with a coil spring (not illustrated). When the supply of electric charges to the rotary solenoid 3 is cut off, the raised piston 2 is caused to descend back into an initial position by the biasing force of the coil spring in a descending direction.

The transparent glass plate 7 holds the nozzle 6. The glass plate 7 is also used as a transmitting member. The glass plate 7 transmits light for cornea deformation detection, light for anterior segment observation, alignment light, and light for corneal thickness measurement. The light for anterior segment observation is light for observing the anterior segment from a frontal direction. The glass plate 7 includes a glass plate 7a disposed on the examinee's eye side, and a glass plate 7b. The glass plate 7a also plays the role for preventing the entry of foreign matter into the internal optical system from the outside. The glass plate 7b forms a side wall of the air compression chamber 11. The transparent glass plate 9 is disposed to the rear of the nozzle 6. The glass plate 9 forms a rear wall of the air compression chamber 11. The glass plate 9 transmits the observing light and the alignment light. At the rear of the glass plate 9, an optical system (observation/alignment optical system) 8 for observation and alignment is disposed, as will be described below. The pressure sensor 12 detects the pressure in the air compression chamber 11. An air-bleeding hole 13 reduces resistance before the piston 2 gains an initial velocity. Thus, a pressure change substantially proportional to time can be obtained during the rise in pressure.

The control system of the tonometer 100 includes a control circuit (a drive controller, a setting switch controller, an alignment detector, a measurement unit, a first measuring unit, a second measuring unit, and a light detector) 20. To the control circuit 20, there are connected a pressure detection processing circuit 21 for the pressure sensor 12; a signal detection processing circuit 22 for a light detector 57 of a corneal shape detecting optical system (cornea deformation detecting optical system) which will be described below; a signal detection processing circuit 28 for a light receiving device 77 for actuation distance detection and corneal thickness measurement; and a signal detection processing circuit 26 for a position detection device 60 for actuation distance detection. To the control circuit 20, there are further connected a signal detection processing circuit 27 for a CCD camera 35, a drive circuit 23 for driving the rotary solenoid 3, and a memory 24 for storing measurement data and the like. The control circuit 20 is also connected to various light sources provided in optical systems depicted in FIG. 3. The various light sources include a light source 30 for illuminating the anterior segment, a light source 40, a light source 45, a light source 50, and a light source 71. The control circuit 20 performs various controls.

Figure 3:
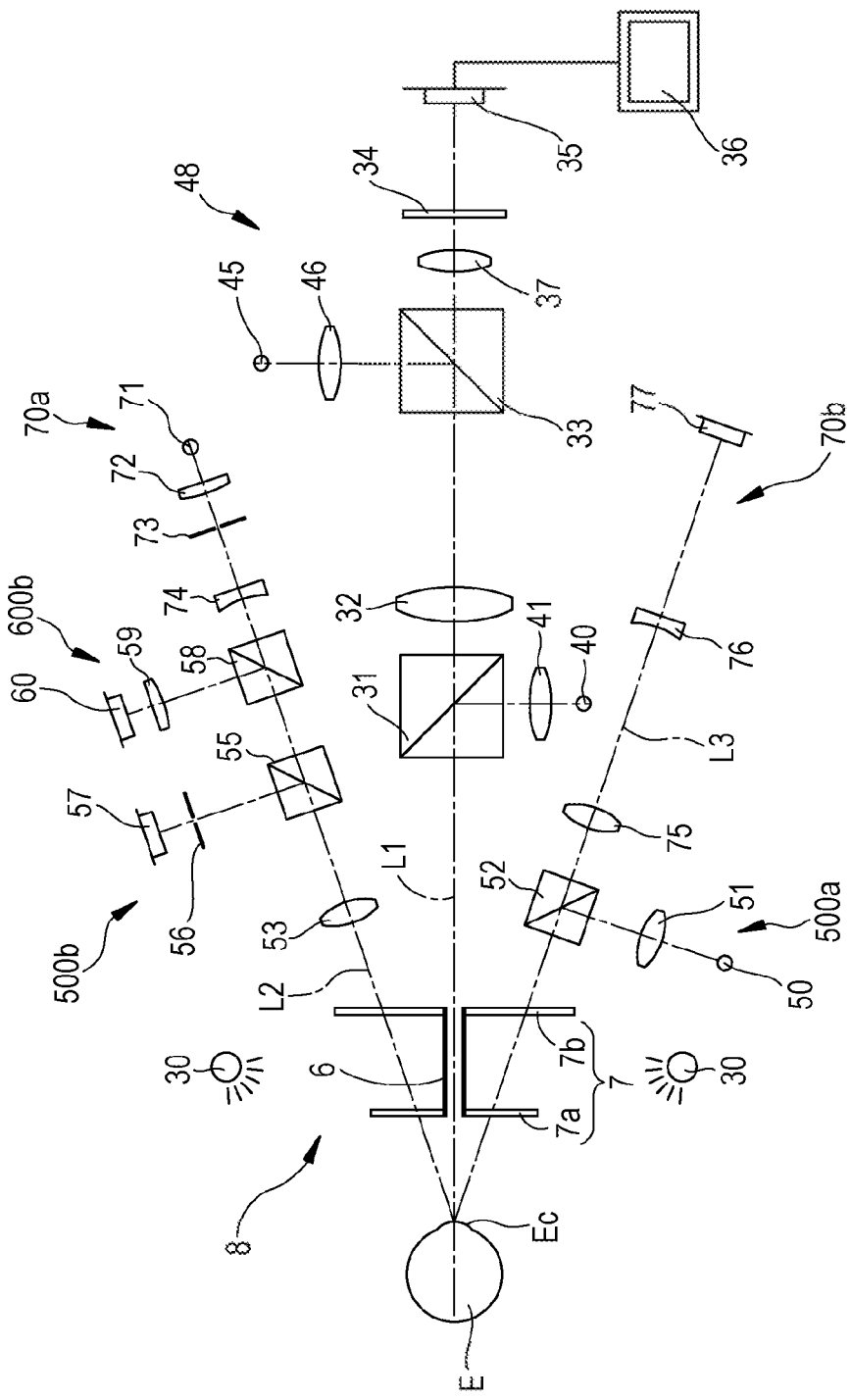
FIG. 3 is a schematic diagram illustrating main parts of an optical system of the apparatus according to the embodiment when viewed from above.

FIG. 3 is a schematic diagram illustrating main parts of an optical system of the tonometer 100 (optical system 8 for observation and alignment) when viewed from above. In the measurement unit 104, for example, the optical systems of the tonometer 100 are disposed. The optical systems include an observing optical system, a detecting optical system, a fixation optical system, a corneal shape detecting optical system, a first actuation distance detecting optical system, a corneal thickness measurement optical system (a second measuring unit), and a second actuation distance detecting optical system.

By illuminating the eye E with light from the light source (e.g., infrared light source) 30, an examinee's eye image is formed on the CCD camera 35 via a beam splitter 31, an objective lens 32, a dichroic mirror 33, an imaging lens 37, and a filter 34. Namely, the optical system including the beam splitter 31 to the CCD camera 35 includes an imaging device. The optical system is used as the observing optical system for observing the anterior segment of the examinee's eye. In this case, an optical axis L1 is used as an observing optical axis.

The filter 34 transmits the light from the light source 30 and also transmits the light from the light source 40 for alignment. However, the filter 34 does not transmit substantially the light from the light source 50 for corneal shape (cornea deformation) detection, which will be described below, or visible light. The light source 50 for corneal shape detection will be described below. The image formed on the CCD camera 35 is displayed on the monitor 36.

The infrared light projected from the alignment light source 40 via the projecting lens 41 is reflected by the beam splitter 31. The reflected light is projected onto the examinee's eye from the front. A cornea raster formed at the corneal apex by the light source 40 forms an image on the CCD camera 35 via the beam splitter 31 to the filter 34. The image thus formed is used for alignment detection in up-down and left-right directions. Namely, the optical system including the beam splitter 31 to the CCD camera 35 includes an imaging device. The optical system is used as the detecting optical system (alignment detector) for detecting an alignment state of the optical systems (or the measurement unit 104) with respect to the examinee's eye in the up-down and left-right directions. In this case, the optical axis L1 is used as an alignment optical axis. According to the present embodiment, the detecting optical system doubles as the observing optical system for observing the anterior segment.

A fixation optical system 48 includes the optical axis L1. The fixation optical system 48 exhibits a fixation target to the eye E from the frontal direction. In this case, the optical axis L1 is used as a fixation optical axis. The fixation optical system 48 includes, for example, a visible light source (fixation light) 45, a projecting lens 46, and the dichroic mirror 33 The fixation optical system 48 projects onto the eye E light for causing the eye E to be fixed in the frontal direction. The visible light source 45 includes, for example, an LED or a laser. The light source 45 may include a pattern light source, such as a point light source, a slit light source, or a ring light source. The light source 45 may also include a two-dimensional display unit, such as a liquid crystal display.

The visible light emitted from the light source 45 is passed through the projecting lens 46, reflected by the dichroic mirror 33, and passed through the objective lens 32. Thereafter, the visible light is projected onto the fundus of the eye E. Thus, the eye E is caused to fixedly view a fixation point in the frontal direction. As a result, the direction of the visual line of the eye E is fixed. The visible light emitted from the light source 45 is converted into a parallel light flux as the light is passed through the projecting lens 46 and the objective lens 32.

The corneal shape detecting optical system (the first measuring unit) includes a light projecting optical system 500a and a light receiving optical system 500b. The corneal shape detecting optical system detects the shape of the cornea Ec (deformed state). The optical systems 500a and 500b are disposed in the measurement unit 104. The optical systems 500a and 500b are three-dimensionally moved by the XYZ drive unit 106. It goes without saying that the optical systems 500a and 500b may be of hand-held type.

The light projecting optical system 500a (the first light projecting optical system) includes an optical axis L3 as a light projecting optical axis. The light projecting optical system 500a irradiates the cornea Ec of the eye E with illuminating light in an oblique direction. The light projecting optical system 500a includes the infrared light source (the first illuminating light source) 50, a collimator lens 51, and a beam splitter 52, for example. The light receiving optical system 500b includes the light detector 57. The light receiving optical system 500b receives reflected light obtained as the illuminating light is reflected by the cornea Ec of the eye E. The light receiving optical system 500b is disposed at a position substantially symmetrical with the light projecting optical system 500a with respect to the optical axis L1. The light receiving optical system 500b (the first light receiving optical system) includes a lens 53, a beam splitter 55, a pinhole plate 56, and the light detector 57 (the first light receiving device), for example. The light receiving optical system 500b forms an optical axis L2 as a light receiving optical axis.

The light emitted from the light source 50 is made into a substantially parallel light flux by the collimator lens 51. After being reflected by the beam splitter 52, the light becomes substantially coaxial (substantially aligned) with the optical axis L3 of the light receiving optical system 70b. The light is projected onto the cornea Ec of the examinee's eye. The light reflected by the cornea Ec becomes substantially coaxial (substantially aligned) with the optical axis L2 of the light projecting optical system 70a. The light projecting optical system 70a and the light receiving optical system 70b will be described below. After passing through the lens 53, the light is reflected by the beam splitter 55. The reflected light is passed through the pinhole plate 56 and then received by the light detector 57. The lens 53 is provided with a coating. The coating has substantially non-transmissive characteristics with respect to the light from the light source 30 and the light source 40. The corneal shape detecting optical system is disposed such that the amount of light received by the light detector 57 is maximized when the examinee's eye is in a predetermined deformed state (such as in a flat state).

In the tonometer 100 according to the present embodiment, the corneal shape detecting optical system is disposed at an angle with respect to the optical axis L1 as the observing optical axis. Thus, a part of the corneal shape detecting optical system can provide a member of the first actuation distance detecting optical system, such as the light source 50 or an optical device, as will be described below. In this way, the configuration of the tonometer 100 can be simplified.

The corneal shape detecting optical system provides a part of the first actuation distance detecting optical system. The light projecting optical system of the first actuation distance detecting optical system provides the light projecting optical system 500a of the corneal shape detecting optical system. The light receiving optical system 600b receives the reflected light from the cornea Ec due to the light source 50. The light receiving optical system 600b includes the lens 53 of the light projecting optical system 500a, a beam splitter 58, a condenser lens 59, and the position detection device 60. The light receiving optical system 600b forms the optical axis L2 as the light receiving optical axis.

Figure 4:
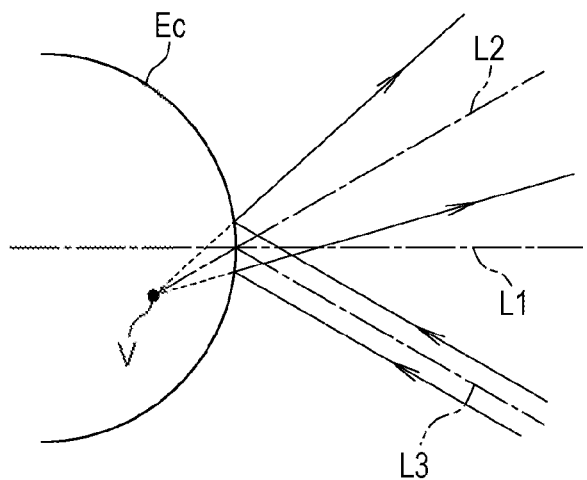
FIG. 4 is a schematic diagram illustrating a target image due to illuminating light reflected by the cornea.

The illuminating light projected by the light source 50 and then reflected by the cornea Ec forms a target image V (see FIG. 4), which is a virtual image of the light source 50. The light of the target image V passes through the lens 53 and the beam splitter 55 and is reflected by the beam splitter 58. The reflected light passes through the condenser lens 59 and enters the position detection device 60, which may be one-dimensional or two-dimensional. The position detection device 60 includes a PSD or a line sensor, for example. As the examinee's eye E (cornea Ec) moves in the actuation distance direction (Z-direction), the target image by the light source 50 also moves on the position detection device 60. Thus, the control circuit 20 acquires actuation distance information based on an output signal from the position detection device 60.

According to the present embodiment, the output signal from the position detection device 60 is utilized for alignment (coarse adjustment) in the actuation distance direction (Z-direction). The light receiving optical system 600b of the first actuation distance detecting optical system has a magnifying power that is not large compared with a magnifying power of the light receiving optical system 70b as will be described below. Thus, the position detection device 60 has a distance detection range in the Z-direction which is larger than a distance detection range of the light receiving device 77. The distance detection range of the position detection device 60 is ±3 mm to 4 mm from an alignment reference position, for example.

The corneal thickness measurement optical system (the second measuring unit) includes the light projecting optical system 70a, the light receiving optical system 70b, and the fixation optical system 48, for example. The corneal thickness measurement optical system is used for measuring the corneal thickness of the examinee's eye E. The light projecting optical system 70a (the second light projecting optical system) provides a part of the corneal shape detecting optical system and the first actuation distance detecting optical system. The optical systems 70a, 70b, and 48 are disposed in the measurement unit 104, as are the optical systems 500a to 600b. The optical systems 70a, 70b, and 48 are three-dimensionally moved by the XYZ drive unit 106.

The light projecting optical system 70a includes the optical axis L2 as a light projecting optical axis. The light projecting optical system 70a obliquely irradiates the cornea Ec of the eye E with illuminating light (measuring light). The light projecting optical system 70a includes the illuminating light source 71 (the second illuminating light source), a condenser lens 72, a light limiting member 73, a concave lens 74, and the lens 53. The lens 53 is shared with the corneal shape detecting optical system. The light source 71 includes a visible light source or an infrared light source (including near-infrared). The light source 71 may include an LED or a laser. The condenser lens 72 condenses light emitted from the light source 71. The light source 50 and the light source 71 emit mutually different wavelengths of light.

The light limiting member 73 is disposed on the optical path of the light projecting optical system 70a. The light limiting member 73 limits the light emitted from the light source 71. The light limiting member 73 is disposed at a position substantially conjugate with the cornea Ec. As the light limiting member 73, for example, a pinhole plate or a slit plate is used. The light limiting member 73 is used as an aperture for allowing some of the light emitted from the light source 71 to pass through while blocking the other portion of the light. The light projecting optical system 70a forms a predetermined patterned light flux on the cornea of the eye E. The patterned light flux is, for example, a spot light flux or a slit light flux.

The light receiving optical system 70b (the second light receiving optical system) includes the light receiving device (a common sensor, the second sensor, a light detector, the second light receiving device) 77. The light receiving optical system 70b receives reflected light of the illuminating light from the front surface and rear surface of the cornea of the eye E. The light receiving optical system 70b is disposed at a position substantially symmetrical with the light projecting optical system 70a with respect to the optical axis L1. The light receiving optical system 70b includes, for example, the light receiving lens 75, the concave lens 76, and the light receiving device 77. The light receiving optical system 70b forms the optical axis L3 as the light receiving optical axis. The light receiving optical system 70b illustrated in FIG. 3 also provides the second actuation distance detecting optical system (alignment detector) for detecting the alignment state with respect to the eye E in the Z-direction.

The light receiving device 77 includes a plurality of photoelectric conversion devices. Each of the plurality of photoelectric conversion devices receives the reflected light from the corneal front surface and rear surface. As the light receiving device 77, for example, a light detecting device such as a one-dimensional line sensor or a two-dimensional area sensor is used. The light receiving optical system 70b of the corneal thickness measurement optical system and of the second actuation distance detecting optical system conducts observation by increasing the magnifying power. Thus, the distance detection range of the light receiving device 77 in the Z-direction becomes narrower than the distance detection range of the position detection device 60. For example, the distance detection range of the light receiving device 77 in the Z-direction is in the range of ±1 mm from the alignment reference position. An output terminal of the light receiving device 77 is connected to the control circuit 20.

When the examinee's eye E (cornea Ec) moves in the actuation distance direction (Z-direction), the reflected light from the cornea Ec due to the light source 71 also moves on the light receiving device 77. Thus, the control circuit 20 obtains the actuation distance information based on an output signal from the light receiving device 77 of the second actuation distance detecting optical system. The control circuit 20 also detects the corneal shape (deformed state) or blinking of the examinee's eye E based on the output signal from the light receiving device 77. Based on the output signal, the control circuit 20 controls the driving of the rotary solenoid 3.

The positional relationship among the optical systems 70a, 70b, and 48 will be described. For example, the optical axis L2 of the light projecting optical system 70a and the optical axis L3 of the light receiving optical system 70b are disposed at substantially symmetrical positions with respect to the optical axis L1 of the fixation optical system 48. The substantially symmetrical positions include, for example, left-right symmetric and up-down symmetric positions.

The light emitted from the illuminating light source 71 is condensed by the condenser lens 72. The condensed light illuminates the light limiting member 73 from behind. The light from the light source 71 is then limited by the light limiting member 73. Thereafter, the limited light is focused (condensed) by the lens 53, forming an image near the cornea Ec. For example, when a pinhole plate is used as the light limiting member 73, a pinhole image is formed near the cornea Ec. When a slit plate is used as the light limiting member 73, a slit image is formed near the cornea Ec. At this time, the light from the light source 71 forms an image in the vicinity of an intersection of the optical axis and the visual axis on the cornea Ec.

When the illuminating light is projected onto the cornea Ec by the light projecting optical system 70a, the reflected light from the cornea Ec due to the illuminating light travels in a direction (opposite direction) symmetric to the projected light flux with respect to the optical axis L1. The reflected light is then focused by the light receiving lens 75, forming an image on the light receiving plane of the light receiving device 77.

Figure 5:
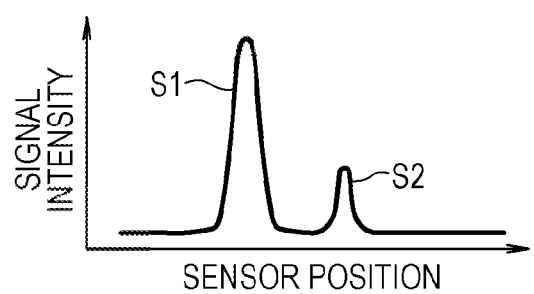
FIG. 5 is a schematic diagram illustrating an example of light receiving signals for reflected light from a corneal front surface and a corneal rear surface received by a light receiving device.
Figure 6:
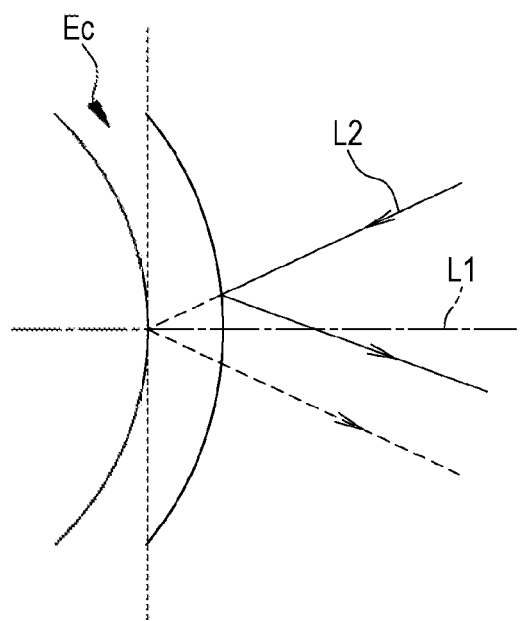
FIG. 6 is a schematic diagram illustrating the optical path of the reflected light from the corneal front surface and the optical path of the reflected light from the corneal rear surface.

FIG. 5 illustrates the output from the light receiving device 77, specifically a first light receiving signal S1 of the reflected light from the front surface (epithelium) of the cornea Ec, and a second light receiving signal S2 of the reflected light from the rear surface (endothelium) of the cornea Ec. Thus, the light receiving signals are detected in response to the reflected light having strong luminance at the front surface (epithelium) and the rear surface (endothelium) of the cornea Ec. As illustrated in FIG. 6, the reflected light (see solid lines) from the front surface of the cornea Ec and the reflected light (see broken lines) from the rear surface of the cornea Ec have different reflected optical paths. Thus, the reflected light from the front surface of the cornea Ec and the reflected light from the rear surface of the cornea Ec form images at different positions on the light receiving device 77.

As described above, according to the present embodiment, the optical systems are disposed to cause substantial coincidence between the light projecting optical axis of both the corneal shape detecting optical system and the first actuation distance detecting optical system and the light receiving optical axis of both the corneal thickness detecting optical system and the second actuation distance detecting optical system. Further, the optical systems are disposed to cause substantial coincidence between the light receiving optical axis of both the corneal shape detecting optical system and the first actuation distance detecting optical system and the light projecting optical axis of both the corneal thickness detecting optical system and the second actuation distance detecting optical system. Namely, the light projecting optical system 500a and the light receiving optical system 70b share the optical axis L3. The light projecting optical system 70a shares the optical axis L2 with the light receiving optical system 500b and the light receiving optical system 600b.

The output light (illuminating light) from the light source 50 is reflected by the beam splitter 52, travels along the optical axis L3, and enters the cornea Ec. The light is then reflected at an angle such that the angle of incidence on the cornea Ec is equal to the angle of reflection, and travels along the optical axis L2. Thus, the output light from the light source 50 is substantially not detected by the light receiving device 77. Similarly, the output light from the light source 71 passes through the beam splitters 58 and 55, proceeds along the optical axis L2, and then enters the cornea Ec. There, the light is reflected at an angle such that the angle of incidence on the cornea Ec is equal to the angle of reflection, and proceeds along the optical axis L3. Thus, the output light from the light source 71 is substantially not detected by the light detector 57 or the position detection device 60.

In this way, the light receiving signal is obtained when the light emitted from the light source 50 is reflected from the cornea Ec and detected by the light detector 57 and the position detection device 60. Thus, the light receiving signal thus obtained can be prevented from being influenced by the light that is emitted from the light source 71 and reflected from the cornea Ec. Similarly, the light receiving signals S1 and S2 are obtained when the light emitted from the light source 71 and reflected from the cornea Ec is detected by the light receiving device 77. Thus, the signals S1 and S2 can be prevented from being influenced by the light emitted from the light source 50 and reflected from the cornea Ec.

The lens 53 is shared by the light receiving optical systems 500b and 600b and the light projecting optical system 70a. The lens 53 is disposed at a position such that the reflected light from the cornea Ec that is due to the light source 50 is condensed at the center of the opening in the pinhole plate 56. The position of the lens 53 is also such that the illuminating light from the light source 71 is condensed at the front surface and rear surface of the cornea Ec.

An operation of the tonometer 100 configured as described above will be described. The examiner has the examinee's eye E placed at a predetermined position and has the examinee gaze the fixation target. By operating the joystick 105 based on the alignment information displayed on the monitor 36, the examiner performs alignment adjustment (adjustment of the position of the measurement unit 104). The alignment adjustment in the up-down and left-right directions is performed by achieving a predetermined relationship between the cornea raster formed by the light source 40 and a reticle (not illustrated) displayed on the monitor 36. The alignment in the up-down and left-right directions may be based on automatic alignment. In this case, the control circuit 20 controls the XYZ drive unit 106 such that the cornea raster by the light source 40 is formed at an alignment position set on the CCD camera 35 (such as an intersection of the optical axis L1 and the imaging plane of the CCD camera 35). In this way, the control circuit 20 causes the measurement unit 104 to be moved to an alignment completed position with respect to the XY-direction.

After the alignment adjustment in the XY-direction is completed, alignment adjustment in the Z-direction is performed. In the alignment adjustment in the Z-direction, the control circuit 20 controls the drive unit 106 on the basis of the actuation distance information. The actuation distance information is obtained from the position detection device 60 and the light receiving device 77. The control circuit 20 causes the measurement unit 104 to be moved toward a predetermined alignment completed position in the Z-direction (automatic alignment).

Before the automatic alignment is started, the examiner performs alignment in the Z-direction. First, the examiner causes the measurement unit 104 to be moved in the Z-direction by operating the joystick 105 such that the light of the target image on the cornea Ec due to the output light from the light source 50 enters the position detection device 60.

When the light of the target image is detected by the position detection device 60, the control circuit 20 causes the measurement unit 104 to be moved in the Z-direction based on the actuation distance information obtained from the position detection device 60. At this time, the measurement unit 104 moves such that the reflected light from the cornea Ec due to the light source 71 enters the range of detection by the light receiving device 77. After the movement is complete, the control circuit 20 causes the measurement unit 104 to be moved in the Z-direction on the basis of the light receiving signal detected by the light receiving device 77 that corresponds to the reflected light from the cornea Ec due to the output light from the light source 71.

Figure 7A:
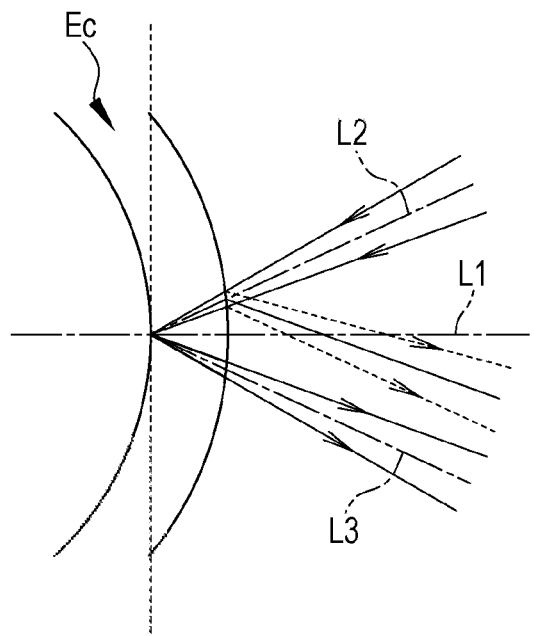
FIGS. 7A and 7B are diagrams each illustrating how the light emitted from a light source is reflected by the cornea.
Figure 7B:
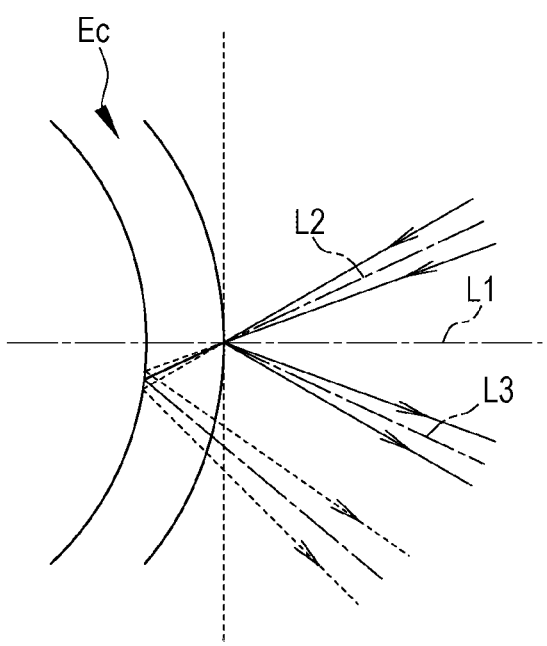
Figure 8A:
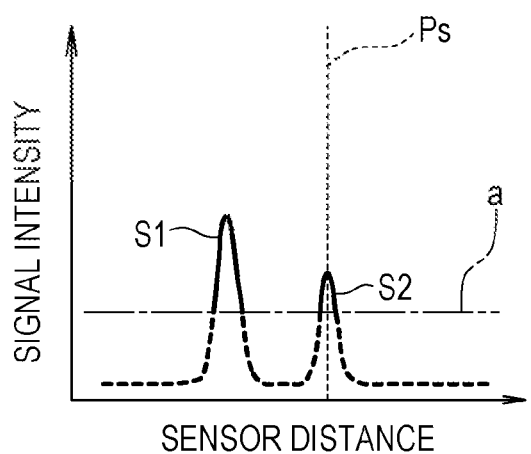
FIGS. 8A and 8B are graphic diagrams illustrating a light receiving signal output from a light receiving device, specifically a part of the light receiving signal corresponding to reflection by the corneal front surface and a part of the light receiving signal corresponding to reflection by the corneal rear surface.
Figure 8B:
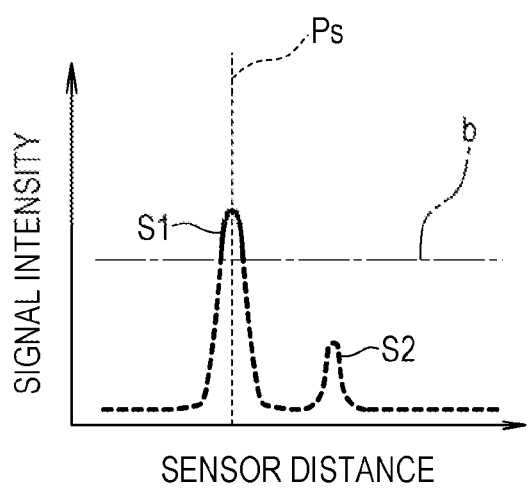

FIGS. 7A and 7B illustrate how the light emitted from the light source 71 is reflected by the cornea Ec. FIGS. 8A and 8B illustrate a part of the light receiving signal output from the light receiving device 77. Specifically, FIGS. 8A and 8B illustrate a part of the first light receiving signal S1 corresponding to the reflected light on the front surface of the cornea Ec, and a part of the second light receiving signal S2 corresponding to the reflected light on the rear surface of the cornea Ec.

As illustrated in FIG. 7A, the control circuit 20, during measurement of the corneal thickness, sets an alignment reference in the vicinity of the corneal rear surface or the corneal rear surface (a second alignment reference). Namely, the control circuit 20 moves the measurement unit 104 to a position such that the output light from the light source 71 that is condensed by the lens 53 is substantially condensed at the rear surface of the cornea Ec.

For example, when measuring the corneal thickness, the control circuit 20 sets a threshold value a for extracting the second light receiving signal S2. As illustrated in FIG. 8A, the control circuit 20 detects the position of a peak of the second light receiving signal S2 extracted as a signal portion with an intensity exceeding the threshold value a. The control circuit 20 controls the drive unit 106 such that the peak of the second light receiving signal S2 is formed at an alignment completed position Ps (such as a center position) set on the light receiving device 77. The threshold value a may be smaller than the peak value of the first light receiving signal S1 and the peak value of the second light receiving signal S2. The threshold value a may be greater than a minimum value between the first light receiving signal S1 and the second light receiving signal S2. This is so that the first light receiving signal S1 and the second light receiving signal S2 can be separately extracted. The magnitude of the threshold value a is experimentally determined, for example.

After the alignment for corneal thickness measurement is complete, the control circuit 20 automatically produces a measurement starting trigger signal. Thus, the control circuit 20 starts corneal thickness measurement. Alternatively, the corneal thickness measurement may be started by the input of a trigger signal by the examiner.

It is now assumed that, as illustrated in FIG. 7B, alignment has been performed such that the output light from the light source 71 is condensed at the front surface of the cornea Ec. In this case, as illustrated in FIG. 8, the second light receiving signal S2 corresponding to the reflection at the rear surface of the cornea Ec as detected is small compared with the first light receiving signal S1 corresponding to the reflection at the front surface of the cornea Ec. As will be described below, the control circuit 20 performs corneal thickness measurement based on the distance between the first light receiving signal S1 and the second light receiving signal S2 (or the peak-to-peak distance of the signals). Thus, when the second light receiving signal S2 is small, measurement accuracy is decreased. Accordingly, in the tonometer 100 according to the present embodiment, the measurement unit 104 moves to a position such that the output light from the light source 71 can be substantially condensed at the rear surface of the cornea Ec so that the second light receiving signal S2 of a large value can be detected during the corneal thickness measurement.

After the trigger signal for starting the measurement is generated, the control circuit 20 calculates the distance (interval) between the first light receiving signal S1 and the second light receiving signal S2 that have been extracted. The light receiving signals are extracted by an edge detection process performed on the luminance distribution, for example. The control circuit 20 may calculate the distance between the two peaks based on the output from the light receiving device 77, and then calculate the corneal thickness based on the calculated distance.

Thereafter, the control circuit 20 converts the calculated distance into a measurement value of the corneal thickness of the eye E by using at least one of a computing expression and a table. The resultant measurement value is stored in the memory 24. The computing expression is generated by an optical simulation, for example, taking into consideration the difference in refractive index between air and the cornea and/or the difference in corneal curvature. The table is generated by calibration using a plurality of known eyes (such as model eyes) with different thicknesses, for example. The computing expression and/or the table may be stored in the memory 24 in advance.

The control circuit 20 may calculate the corneal thickness a plurality of times (such as 10 times) by acquiring the light receiving signal from the light receiving device 77 a plurality of times. Then, the control circuit 20 may store an average value of the corneal thickness in the memory 24 as the corneal thickness measurement value.

After the corneal thickness measurement is completed, the control circuit 20 performs alignment in the Z-direction for eye pressure measurement. As illustrated in FIG. 7B, the control circuit 20, when measuring the eye pressure, sets an alignment reference (a first alignment reference) on the front surface of the cornea. Namely, the control circuit 20 moves the measurement unit 104 to a position such that the output light from the light source 71 that is condensed by the lens 53 is substantially condensed at the front surface of the cornea Ec.

For example, the control circuit 20 switches the setting from the threshold value a to a threshold value b. The threshold value b is a threshold value for extracting the first light receiving signal S1. As illustrated in FIG. 8B, the control circuit 20 detects the position of the peak of the first light receiving signal S1 extracted as a signal portion with an intensity exceeding the threshold value b. The control circuit 20, during eye pressure measurement, moves the measurement unit 104 to a position such that the peak of the first light receiving signal S1 is formed at the alignment completed position Ps set on the light receiving device 77. Thus, the alignment in the Z-direction is performed. The threshold value b may be smaller than the peak value of the first light receiving signal S1, and greater than the peak value of the second light receiving signal S2. This is in order to extract the first light receiving signal S1. The magnitude of the value b may be experimentally determined. During the eye pressure measurement, the second light receiving signal S2 due to the reflected light from the rear surface of the cornea Ec is substantially not used for the measurement. Thus, the alignment may be performed based on the first light receiving signal, which is relatively strongly detected compared with the second light receiving signal S2.

When switching from the state in which the alignment for corneal thickness measurement is performed to the alignment in the Z-direction for eye pressure measurement, the control circuit 20 changes the alignment reference from the second alignment reference to the first alignment reference. Thereby, the measurement unit 104 is driven in a direction away from the examinee's eye E.

The control circuit 20 or the corneal thickness measurement optical system may generate a measurement completion signal at the end of each film thickness measurement. The control circuit 20 may be configured to switch the alignment reference from the second alignment reference to the first alignment reference in response to the measurement completion signal.

The control circuit 20 may use a reflection signal from the corneal rear surface and a reflection signal from the corneal front surface which are included in the reflection signal from the cornea output from the light receiving device 77 for switching the alignment reference.

In response to the change in the alignment reference, the control circuit 20 controls the drive unit 106 such that the measurement unit 104 moves in a direction away from the corneal thickness measurement position for the examinee's eye E by the corneal thickness measurement value that has been previously measured. Thereby, the condensed position of the light from the light source 71 reaches the vicinity of the corneal front surface. Thereafter, the control circuit 20 causes the measurement unit 104 to be moved in the Z-direction based on the first light receiving signal S1 as described above. By such control, the time for alignment adjustment can be decreased.

The control circuit 20 may detect the alignment state of the measurement unit 104 with respect to the first alignment reference during the alignment using the first alignment reference. The control circuit 20 may measure the eye pressure and corneal thickness of the examinee's eye successively.

The control circuit 20 starts electric current supply to the rotary solenoid 3 before completion of alignment. The control circuit 20 controls the driving of the rotary solenoid 3 such that liquid is sprayed onto the cornea of the examinee's eye after the alignment operation in the Z-direction using the light receiving device 77 is completed. The control circuit 20 controls the driving of the rotary solenoid 3 by supplying the rotary solenoid 3 with the electric charges as operation-enabling driving energy via the drive circuit 23.

When the rotary solenoid 3 is supplied with the electric charges, the piston 2 rises. The piston 2 compresses the air in the air compression chamber 11. The compressed air is sprayed from the nozzle 6 toward the cornea of the examinee's eye E. The cornea is gradually deformed as the examinee's eye E is sprayed with the compress air. The reflected light from the cornea due to the light projected by the light source 50 enters the light detector 57. The shape of the cornea (deformed state) is detected from the output signal from the light detector 57.

As the compress air is sprayed, the cornea of the examinee's eye is gradually deformed. When the cornea of the examinee's eye reaches an applanation state, the amount of light that enters the light detector 57 is maximized. The control circuit 20 determines the eye pressure value when the cornea of the examinee's eye is in the applanation state, based on the output signal from the pressure sensor 12.

The control circuit 20 corrects the eye pressure measurement value for the examinee's eye based on the corneal thickness measured by the corneal thickness measurement optical system. In this case, the corneal thickness measurement value can be substituted into a regression equation expressing the correlation between the corneal thickness and the amount of measurement error from the true eye pressure. The regression equation is generated empirically, for example. The control circuit 20 further modifies the eye pressure measurement value in light of measurement error. In this way, the control circuit 20 can correct the eye pressure value.

Thereafter, the control circuit 20 displays the corrected eye pressure value and the corneal thickness measurement value on the monitor 36. After a predetermined number (such as 3) of measurement values from which measurement error has been eliminated are obtained, the control circuit 20 ends the eye pressure measurement.

In the conventional tonometer, the alignment reference for the Z-direction is constant. On the other hand, in the tonometer 100 according to the present embodiment, the alignment reference for the Z-direction is switched between corneal thickness measurement and eye pressure measurement. Thus, the tonometer 100 can accurately measure the corneal thickness while maintaining eye pressure measurement accuracy.

The switching of the two threshold values between alignment for corneal thickness measurement and alignment for eye pressure measurement simplifies the extraction process and the peak detection process for the first light receiving signal S1 and the second light receiving signal S2.

In the foregoing description, the output signal from the position detection device 60 of the first actuation distance detecting optical system is utilized for the coarse adjustment of alignment in the Z-direction. However, this is merely an example, and the control circuit 20 may perform final adjustment (fine adjustment) of alignment in the Z-direction based on the output signal from the position detection device (the first sensor) 60 at the time of eye pressure measurement. The eye pressure measurement according to the present embodiment may involve spraying a liquid onto the examinee's eye E virtually simultaneously with the establishment of alignment (immediately after completion of alignment). This is because the examinee's eye E may possibly be moved by the examinee's reflective evasive behavior upon spraying of the liquid. In this case, final adjustment (fine adjustment) of alignment may be performed based on an output signal from a device with high response speed. At the time of corneal thickness measurement, the reflection signal from the corneal rear surface is used. Thus, the output from the light receiving device 77 is used for alignment. In this case, the control circuit 20 may change the sensor used from the light receiving device 77 to the position detection device 60 when switching the alignment reference from the second alignment reference to the first alignment reference.

According to the foregoing embodiment, two threshold values are used for the extraction process for the light receiving signals S1 and S2. However, this is merely an example, and a single threshold value may be used. For example, the first light receiving signal S1 and the second light receiving signal S2 can be extracted by using the single threshold value a. In this case, at the time of corneal thickness measurement, the control circuit 20 performs alignment such that, of the extracted two signals, the peak of the light receiving signal detected to the left of the light receiving device 77 is disposed at a predetermined position on the light receiving device 77. At the time of eye pressure measurement, the control circuit 20 performs alignment such that, of the extracted two signals, the peak of the light receiving signal detected to the right of the light receiving device 77 is disposed at a predetermined position on the light receiving device 77.

Thus, the alignment reference may be switched between the corneal front surface and the corneal rear surface. In this case, the first light receiving signal S1 corresponding to the reflected light from the corneal front surface and the second light receiving signal S2 corresponding to the reflected light from the corneal rear surface may be discriminated based on the positional relationship between the two light receiving signals S1 and S2 with intensities exceeding the threshold value that are detected by the light receiving device 77. The alignment reference may be switched between corneal thickness measurement and eye pressure measurement.

When the signal intensity of the reflected light from the cornea Ec due to the light source 71 is too large, the signal intensity may be prevented from leaving outside the detectable range of the light receiving device 77. For this purpose, the control circuit 20 may adjust (modify) the amount of light from the light source 71 or the gain of the light receiving device 77 between the case where the alignment reference is aligned with the corneal front surface and the case where the alignment reference is aligned with the corneal rear surface.

When the signal intensity of the reflected light from the cornea Ec due to the light source 71 is large and exceeds an upper limit of the detectable range of the light receiving device 77, an assumed peak position may be calculated on the basis of the light receiving signal detected within the detectable range. In this case, the control circuit 20 can perform alignment in the Z-direction such that the calculated peak position is substantially aligned with the alignment completed position Ps. Thus, the alignment in the Z-direction can be achieved without switching the amount of light from the light source 71 or the gain of the light receiving device 77 between the case where the alignment reference is aligned with the corneal front surface and the case where the alignment reference is aligned with the corneal rear surface as described above.

The control circuit 20 may switch the allowable range for alignment adjustment in the Z-direction between corneal thickness measurement and eye pressure measurement.

The embodiment of the present disclosure is not limited to the tonometer 100. The present disclosure may be applied to an apparatus that measures the corneal thickness and an eye characteristic other than the corneal thickness.

In the tonometer 100 according to the present embodiment, the optical systems are disposed to cause substantial coincidence between the light projecting optical axis of both the corneal shape detecting optical system and the first actuation distance detecting optical system and the light receiving optical axis of both the corneal thickness detecting optical system and the second actuation distance detecting optical system. Further, in the tonometer 100 according to the present embodiment, the optical systems are disposed to cause substantial coincidence between the light receiving optical axis of both the corneal shape detecting optical system and the first actuation distance detecting optical system and the light projecting optical axis of both the corneal thickness detecting optical system and the second actuation distance detecting optical system.

Thus, the tonometer 100 can perform corneal thickness measurement and eye pressure measurement while the light sources 50 and 71 are turned on simultaneously (i.e., the examinee's eye is irradiated with the light from the light source 50 (the first illuminating light) and the light from the light source 71 (the second illuminating light) simultaneously when the eye pressure is measured). Accordingly, the light sources 50 and 71 need not be turned on and off repeatedly for each measurement. The tonometer 100 can also detect, by using the light receiving device 77, the reflected light from the cornea Ec due to the light source 71 when the cornea Ec is deformed by the air from the nozzle 6 during eye pressure measurement. The resultant light receiving signal output from the light receiving device 77 at the time of cornea deformation can be used for correcting the eye pressure value, for example. For example, the hardness and/or elasticity of the eye can be determined based on the amount of deformation in corneal thickness due to the spraying of air. The hardness and elasticity of the eye can be used for correcting the eye pressure value.

In the foregoing description, that "the alignment reference is aligned with the corneal front surface" or "the alignment reference is aligned with the corneal rear surface" is not limited to the aligning of the alignment reference with the corneal front surface or the corneal rear surface in a strict sense. Certain effects can be obtained even by aligning the alignment reference in the vicinity of the corneal front surface or in the vicinity of the corneal rear surface. The alignment reference may be shifted to the left or right of the light receiving signals S1 and S2 (i.e., to the front or rear of the corneal front surface or the corneal rear surface).

For example, the control circuit 20 shifts the alignment reference toward the corneal rear surface from the first light receiving signal S1 corresponding to the corneal front surface by a predetermined distance at the time of corneal thickness measurement. In this case too, the second light receiving signal S2 can be more strongly detected than when the alignment reference is aligned with the corneal front surface.

For example, the control circuit 20 aligns the alignment reference during corneal thickness measurement at the central position between the peak value of the first light receiving signal S1 and the peak value of the second light receiving signal S2. In this case too, the corneal thickness can be accurately measured compared with the case where the alignment reference is aligned with the peak value of the first light receiving signal S1 at the time of corneal thickness measurement.

In the above configuration, the present disclosure can be also applied to a non-contact type ultrasonic tonometer that measures the eye pressure of the examinee's eye using ultrasound. The non-contact type ultrasonic tonometer includes, for example, a transmitting unit that irradiates the cornea of the examinee's eye with ultrasound, and a first detector that detects a reflection signal from the corneal front surface of the examinee's eye by using ultrasound. The non-contact type ultrasonic tonometer measures the eye pressure of the examinee's eye in a non-contact manner based on a signal from the first detector using ultrasound.

According to the present embodiment, when alignment is positioned such that the output light from the light source 71 is condensed at the front surface of the cornea Ec, the second light receiving signal S2 corresponding to the reflection by the rear surface of the cornea Ec as detected becomes smaller than the first light receiving signal S1 corresponding to the reflection by the front surface of the cornea Ec, as illustrated in FIG. 8B. During corneal thickness measurement, alignment may be positioned such that the output light from the light source 71 is substantially condensed at the rear surface of the cornea Ec, so that the second light receiving signal S2 can be increased when detected.

The non-contact type tonometer according to the present embodiment may include the following first to twelfth non-contact type tonometers.

A first non-contact type tonometer comprises: a measurement unit (which is relatively moved by a moving mechanism with respect to an examinee's eye) including a first measurement unit for measuring an eye pressure of the examinee's eye in a non-contact manner, and a second measurement unit for measuring a corneal thickness of the examinee's eye in a non-contact manner; an alignment detector for detecting an alignment state of the measurement unit in a front-rear direction with respect to the cornea of the examinee's eye; a drive controller for driving the moving mechanism based on a result of detection by the alignment detector; and a setting switch controller for switching an alignment reference set on the cornea for the detecting of the alignment state by the alignment detector between a first alignment reference for the measuring of the eye pressure by the first measurement unit and a second alignment reference (that is set closer to a corneal rear surface than the first alignment reference) for the measuring of the corneal thickness by the second measurement unit.

A second non-contact type tonometer is the first non-contact type tonometer, wherein the setting switch controller sets the first alignment reference at a corneal front surface and sets the second alignment reference at the corneal rear surface or in the vicinity of the corneal rear surface.

A third non-contact type tonometer is the first non-contact type tonometer, wherein the drive controller moves the measurement unit toward the alignment reference on the cornea.

A fourth non-contact type tonometer is the first non-contact type tonometer, wherein the setting switch controller switches the second alignment reference to the first alignment reference in response to a measurement completion signal from the second measurement unit.

A fifth non-contact type tonometer is the fourth non-contact type tonometer, wherein the drive controller moves the measurement unit in a direction away from the examinee's eye and toward the first alignment reference after the switching in response to the measurement completion signal, and wherein the alignment detector detects the alignment state with respect to the first alignment reference. Thus, the measurement unit measures the eye pressure and the corneal thickness of the examinee's eye successively.

A sixth non-contact type tonometer is the first non-contact type tonometer, wherein the alignment detector uses an identical common sensor during the detection of the alignment state for measuring the eye pressure and during the detection of the alignment state for measuring the corneal thickness, and discriminates, for switching the alignment reference, between a reflection signal from the corneal rear surface and a reflection signal from the corneal front surface which are included in a reflection signal from the cornea that is output from the common sensor.

A seventh non-contact type tonometer is the first non-contact type tonometer, wherein the alignment detector uses different sensors during the detection of the alignment state for measuring the eye pressure and during the detection of the alignment state for measuring the corneal thickness, and changes the sensors for switching the alignment reference.

An eighth non-contact type tonometer is the first non-contact type tonometer, wherein the alignment detector includes a light detector that detects a reflection signal from the cornea by receiving reflected light from the cornea of the examinee's eye, wherein the alignment state with respect to the corneal front surface is detected by detecting a position of the reflected light from the corneal front surface when measuring the eye pressure with the first measurement unit, and the alignment state with respect to a corneal rear surface is detected by detecting a position of the reflected light from the corneal rear surface during measurement of the corneal thickness with the second measurement unit.

A ninth non-contact type tonometer is the first non-contact type tonometer, wherein the first measurement unit includes:

a liquid spraying unit that sprays a liquid onto the cornea of the examinee's eye via a nozzle; a first light projecting optical system that includes a first illuminating light source for irradiating the cornea of the examinee's eye with first illuminating light in an oblique direction; and a first light receiving optical system that includes a first light receiving device for detecting a deformed shape of the cornea deformed by the liquid spraying unit, by receiving the first illuminating light reflected by a corneal front surface of the examinee's eye, wherein: the second measurement unit includes a second light projecting optical system that includes a second illuminating light source for irradiating the cornea of the examinee's eye with second illuminating light in an oblique direction, and a second light receiving optical system that includes a second light receiving device for receiving reflected light from the corneal front surface and the corneal rear surface of the examinee's eye; the first light projecting optical system has an optical axis aligned with an optical axis of the second light receiving optical system; and the first light receiving optical system has an optical axis aligned with an optical axis of the second light projecting optical system.

A tenth non-contact type tonometer is the ninth non-contact type tonometer, wherein, when measuring the eye pressure, the first illuminating light source and the second illuminating light source irradiate the examinee's eye with the first illuminating light and the second illuminating light simultaneously.

An eleventh non-contact type tonometer is the ninth non-contact type tonometer, wherein, when measuring the eye pressure of the examinee's eye with the first measurement unit, the second light receiving device receives the cornea reflected light due to the illuminating light from the second illuminating light source, the cornea reflected light including the reflected light reflected by the corneal front surface and the corneal rear surface deformed by the liquid spraying unit.

A twelfth non-contact type tonometer is the ninth non-contact type tonometer, comprising an optical device that makes the first illuminating light from the first illuminating light source into parallel light, wherein the optical device is shared with the second light receiving optical system, the optical device causing the cornea reflected light due the illuminating light from the second illuminating light source to be condensed at the second light receiving device.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A non-contact type tonometer comprising: a measurement unit including a first measuring unit configured to measure an eye pressure of an examinee's eye in a non-contact manner and a second measuring unit configured to measure a corneal thickness of the examinee's eye in a non-contact manner;
a moving mechanism configured to cause relative movement of the measurement unit with respect to the examinee's eye;
a drive controller configured to drive the moving mechanism for aligning the measurement unit;
a setting switch controller configured to switch an alignment reference on the cornea used for aligning the measurement unit between a first alignment reference and a second alignment reference,
the first alignment reference is a reference for measuring the eye pressure with the first measuring unit,
the second alignment reference is a reference for measuring the corneal thickness with the second measuring unit and set closer to a corneal rear surface than the first alignment reference, and
the setting switch controller sets the first alignment reference on a corneal front surface of the examinee's eye, and sets the second alignment reference on the corneal rear surface or in the vicinity of the corneal rear surface, and
a first sensor configured to detect the position of the measurement unit during alignment using the first alignment reference; and
a second sensor configured to detect the position of the measurement unit during alignment using the second alignment reference, wherein
the drive controller changes the sensor used upon switching of the alignment reference.

2. The non-contact type tonometer according to claim 1, wherein
the drive controller sets the position of the measurement unit in response to the alignment reference.

3. The non-contact type tonometer according to claim 1, further comprising
a common sensor configured to detect the position of the measurement unit during alignment using the first alignment reference and the second alignment reference, wherein
the setting switch controller uses a reflection signal from the corneal rear surface and a reflection signal from the corneal front surface for the switching of the alignment reference, the reflection signals being included in a reflection signal from the cornea that is output from the common sensor.

4. The non-contact type tonometer according to claim 1, further comprising
a light detector configured to detect a condensed position of output light from a light source on the cornea by receiving reflected light obtained due to reflection of the output light by the cornea of the examinee's eye, wherein
the drive controller, during measurement of the corneal thickness, moves the measurement unit to a position such that the output light from the light source is substantially condensed at the corneal rear surface, and, when measuring the eye pressure, moves the measurement unit to a position such that the output light from the light source is substantially condensed at the corneal front surface.

5. The non-contact type tonometer according to claim 1, wherein
the setting switch controller switches the alignment reference from the second alignment reference to the first alignment reference in response to a measurement completion signal from the second measuring unit.

6. The non-contact type tonometer according to claim 5, wherein the drive controller causes the measurement unit to be moved in a direction away from the examinee's eye in response to the first alignment reference after the switching; and the measurement unit measures the eye pressure and the corneal thickness of the examinee's eye successively.

7. The non-contact type tonometer according to claim 1, wherein the first measuring unit includes a liquid spraying unit configured to spray a liquid onto the cornea of the examinee's eye via a nozzle, a first light projecting optical system that includes a first illuminating light source for irradiating the cornea of the examinee's eye with first illuminating light in an oblique direction, and a first light receiving optical system that includes a first light receiving device and that detects a deformed shape of the cornea deformed by the liquid spraying unit, by receiving the first illuminating light reflected by the corneal front surface of the examinee's eye, the second measuring unit includes a second light projecting optical system including a second illuminating light source for irradiating the cornea of the examinee's eye with second illuminating light in an oblique direction, and a second light receiving optical system including a second light receiving device for receiving reflected light from the corneal front surface and reflected light from the corneal rear surface of the examinee's eye, the first light projecting optical system and the second light receiving optical system have substantially aligned optical axes, and the first light receiving optical system and the second light projecting optical system have substantially aligned optical axes.

8. The non-contact type tonometer according to claim 7, wherein the first light projecting optical system includes an optical device for making the first illuminating light from the first illuminating light source into parallel light, the second light receiving optical system shares the optical device with the first light projecting optical system, and the optical device causes the reflected light from the cornea due to the illuminating light from the second illuminating light source to be condensed at the second light receiving device.

9. The non-contact type tonometer according to claim 7, wherein during measurement of the eye pressure, the examinee's eye is irradiated with the first illuminating light and the second illuminating light simultaneously.

10. The non-contact type tonometer according to claim 9, wherein during measurement of the eye pressure, the second light receiving device receives the reflected light due to the second illuminating light reflected by the front surface and the rear surface of the cornea deformed by the liquid spraying unit.

\* \* \* \* \*